US00PP07930P

United States Patent [19]

Hanes

[11] Patent Number: Plant 7,930

[45] Date of Patent: Aug. 4, 1992

[54] GERANIUM NAMED AMERICANA ROSE

[75] Inventor: Mitchell Hanes, Morgan Hill, Calif.

[73] Assignee: Goldsmith Seeds, Inc., Gilroy, Calif.

[21] Appl. No.: 645,725

[22] Filed: Jan. 25, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new and distinct Geranium cultivar particularly distinguished by its rose and rose red bicolored semi-double flowers on large umbels, and its fast-rooting and compact bush growth habit.

2 Drawing Sheets

BACKGROUND OF THE INVENTION

The present invention comprises a new and distinct cultivar of Geranium, botanically known as *Pelargonium hortorum* Bailey. The new cultivar is propagated from a seedling resulting from the cross of a seed parent Disco (U.S. Plant Pat. No. 5,930) and the pollen parent Blues (U.S. Plant Pat. No. 5,373).

American Rose is a product of a planned breeding program intended to create new geranium cultivars with rose colored flowers with a distinct deeper colored rose red spot at the base of each petal, semi-double flower form, green foliage, vigorous growth and superior cutting productivity.

The new cultivar was created in 1988 in Gilroy, Calif. and has been repeatedly asexually reproduced by cuttings in Gilroy, Calif. and Guatemala over a two year period. It has also been trialed at Okemos, Mi. It has been found to retain its distinctive characteristics through successive propagations; and this novelty appears to be firmly fixed.

DESCRIPTION OF THE DRAWING

This new geranium plant is illustrated by the accompanying photographic drawings of which.

DESCRIPTION OF THE NEW CULTIVAR

Figure 1:
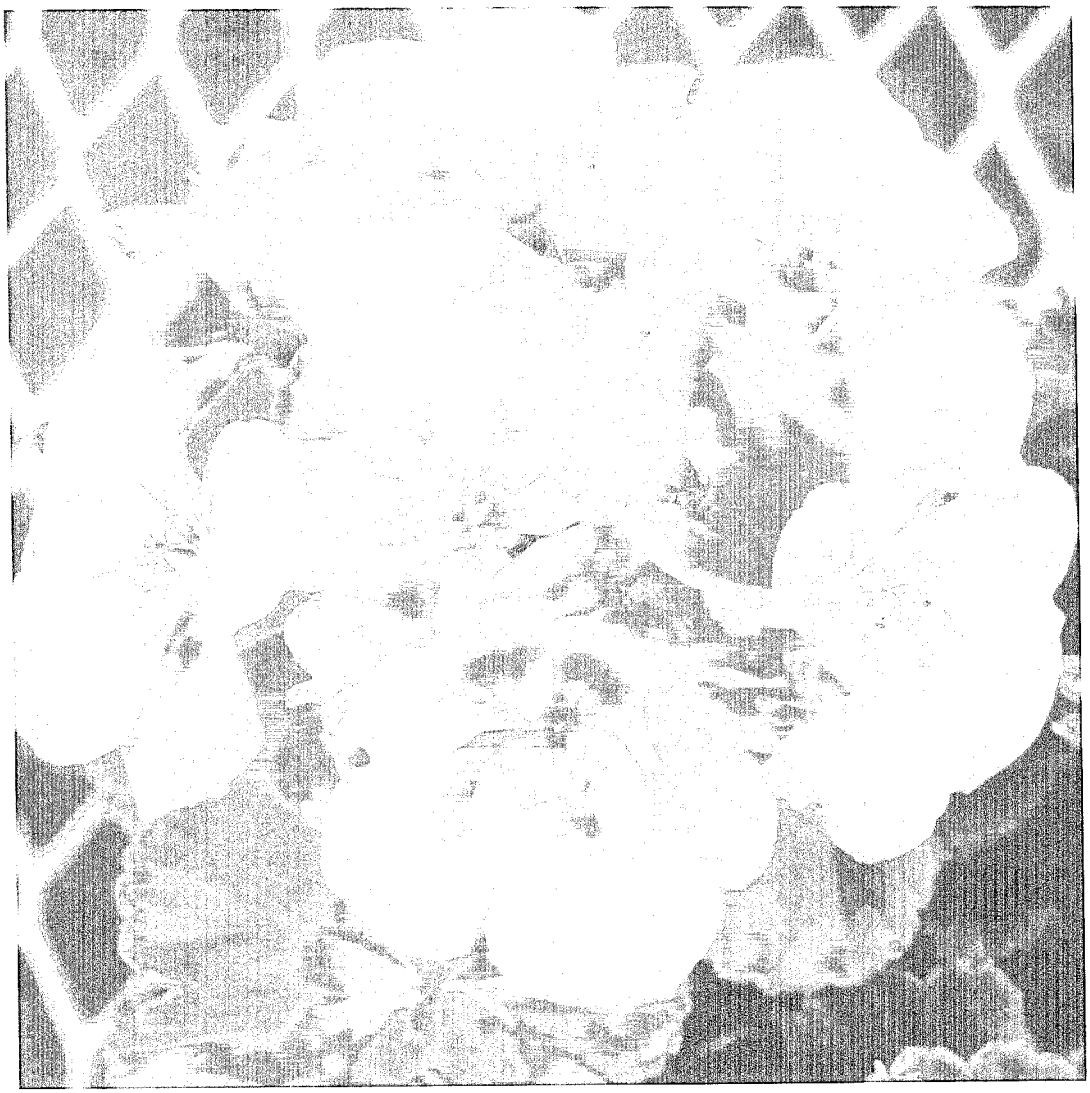
FIG. 1 shows blooms, buds, and foliage of the plant in full color, the colors shown being as true as can be reasonably obtained by conventional photographic procedures.
Figure 2:
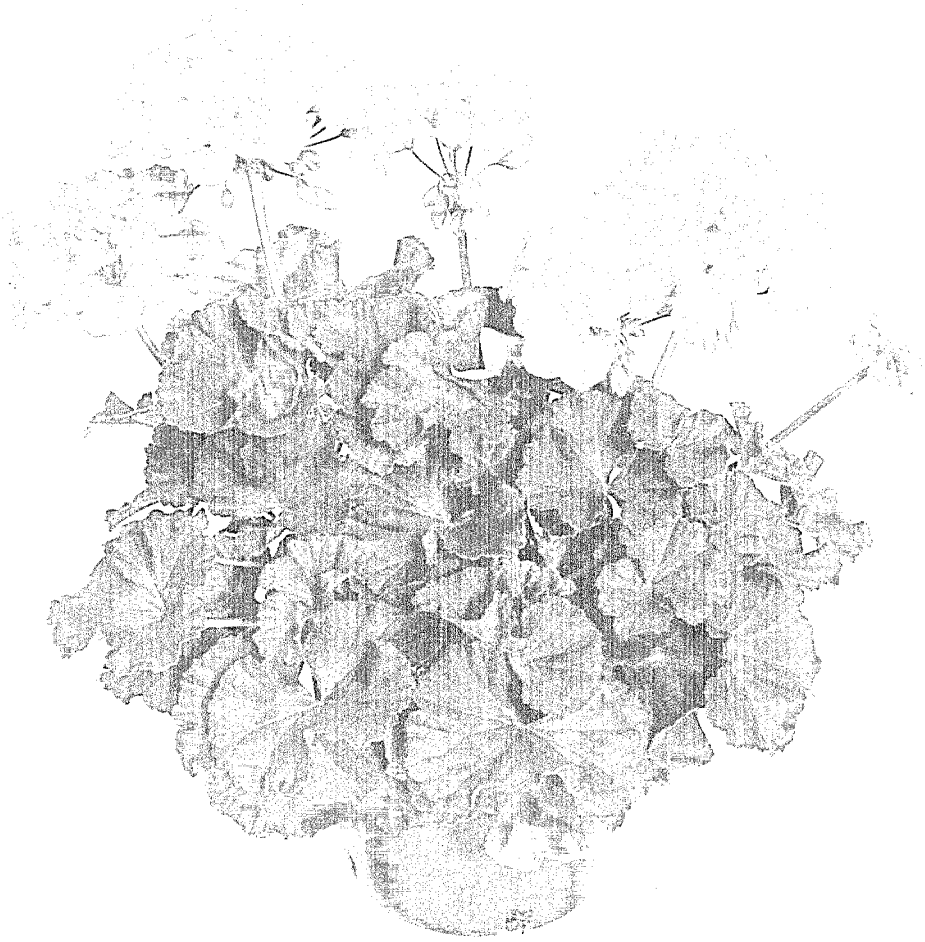
FIG. 2 is a view of a potted plant of this new variety intended only to illustrate its growth habit.

The following detailed description set forth the distinctive characteristics of this new Geranium cultivar. The data which defines these characteristics were collected from asexual reproductions carried out in Gilroy, Calif. The plant history was taken on six week plants, blossomed under natural light in a greenhouse and color readings were taken indoors under 100 candles of cool, white fluorescent light. Color references are primarily to The R.H.S. Colour Chart of The Royal Horticultural Society of London (R.H.S.).

THE PLANT

Classification:

*Botanical.*—*Pelargonium hortorum* Bailey.

*Commercial.*—Zonal Geranium.

Form: Compact bush.

Height: Ten to twelve cm., as a 5½ inch pot plant, excluding blooms.

Growth: Compact bush being very fast-rooting.

Strength: Very sturdy and not susceptible to wind or rain damage. Good shipping ability as rooted or unrooted cuttings.

Foliage: Abundant quantity.

Leaves:

*Size.*—Diameter about 8 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 2 to 2.5 cm. long.

*Color.*—Upperside: Green with light zonation on the outside edge of the younger leaves. Underside: Lighter green color without zonation. Ribs and veins not prominently different from upper surface.

*Petioles.*—About 3.5 to 4.5 cm. in length.

THE BUD

Size:

*Diameter.*—About 8 mm.

Length: About 2.5 cm. to 3.0 cm. at time of bud opening.

Shape: Pointed ovoid.

Color: Of petals when sepals first divide, R.H.S. 54-B.

Sepals: Five in number, flat behind petals. Pointed linear lanceolate, R.H.S. 143-C in an open flower.

THE FLOWER

Blooming habit: Continuous throughout the year.

Size: Approximately 4.5 cm. diameter, 1 cm. deep, irregularly radially symmetrical.

Form: Cup-shaped when bloom first opens, later flattening to shallow cup shape with maturity.

Petals: Five imbricate outer petals, 2.2–2.6 cm. wide and approximately 2.3 cm. long. Three to five inner smaller petaloids of varying shape. The outer petals are bicolored, having a rose red spot R.H.S. 57-A near the center of the petal with the rest of the petal being R.H.S. 68-A. The two upper petals also have a white patch at the basal end. The inner petaloids are R.H.S. 68-A. The veins are not significantly different in color. Underside of petals are lighter fading to whiteish with the veins being darker than the surrounding petal. Petals and petaloids soft and satiny.

Pedicel: Approximately 3.5 cm. in length.
Persistence: Nonshattering flower.

INFLORESCENSE

Type: An umbel composed of approximately 35 flowers, erect or laterally ascending, the umbel having a diameter of about 9–11 cm.

Peduncle: Approximately 7.0–8.5 cm. in length, green in color.

REPRODUCTIVE ORGANS

Stamens:

*Anthers.*—Eight to nine positioned level with or below the mature stigma, light red prior to anthesis.

*Filaments.*—White near base and mid length, graduating to dull red near anther.

*Pollen.*—Orange in color.

Pistil:

*Number.*—One.

*Length.*—Approximately 4 mm.

*Stigma.*—Five linear lobes of near equal length, curling back toward ovary, purplish-red.

*Style length.*—About 2.5–3.0 mm., color: purplish red.

*Ovaries.*—At anthesis, densely pubescent with white hairs, oblong. Green drying to a light brown at maturity.

*Fruit.*—Partially fertile.

I claim:

1. A new and distinct Geranium cultivar substantially as herein shown and described, that is characterized by: green foliage, rose and rose-red bicolored semi-double flowers on large umbels, the plant being fast-rooting and having a compact bush growth habit.

* * * * *